United States Patent [19]
Castellana et al.

[11] 4,050,449
[45] Sept. 27, 1977

[54] APPARATUS FOR EXERCISING MUSCLES OF A FEMALE PATIENT'S PELVIC DIAPHRAGM

[75] Inventors: Frank S. Castellana, Bronx; John C. Byrne, Larchmont, both of N.Y.; Charles E. Huckaba, Washington, D.C.

[73] Assignee: Medical Products Development Corporation, Larchmont, N.Y.

[21] Appl. No.: 661,104

[22] Filed: Feb. 25, 1976

[51] Int. Cl.² .............................................. A61B 5/00
[52] U.S. Cl. ...................................... 128/2 S; 128/79
[58] Field of Search ................. 128/24 R, 79, 2 S, 64, 128/344, 343, 2 R

[56] References Cited

U.S. PATENT DOCUMENTS

| | | | |
|---|---|---|---|
| 1,764,838 | 6/1930 | Horne | 128/64 |
| 2,507,858 | 5/1950 | Kegel | 128/2 S |
| 2,734,508 | 2/1956 | Kozinski | 128/79 UX |
| 3,428,046 | 2/1969 | Remer et al. | 128/344 X |
| 3,598,106 | 8/1971 | Buning | 128/2 R |
| 3,640,284 | 2/1972 | DeLangis | 128/79 UX |

FOREIGN PATENT DOCUMENTS 71,570  10/1893  Germany .............................. 128/344

Primary Examiner—Lawrence W. Trapp
Attorney, Agent, or Firm—Charles E. Baxley

[57] ABSTRACT

An apparatus for exercising muscles of a female patient's pelvic diaphragm, most particularly vaginal wall muscles. A slickened elastomeric elongated balloon with a cylindrical wall and a first closed end is provided. Latex for example is a suitable elastomeric material for this application. The cylindrical wall has sufficient rigidity for the balloon to be inserted closed endwise into the patient's vagina, without need for any stem member. The second end of the balloon reduces in section to form a shoulder and a tube adapted to extend out of the patient's vagina. A collar surrounds the tube and abuts the shoulder so that the patient can manually hold the balloon in her vagina. In an alternate embodiment, the tube is stiffened. The balloon may be filled with a fluid, such as air, another gas or a liquid (at atmospheric or superatmospheric pressures) and measurements of pressures in the balloon index exertions of the muscles of the patients' pelvic diaphragm.

7 Claims, 7 Drawing Figures

U.S. Patent  Sept. 27, 1977  4,050,449
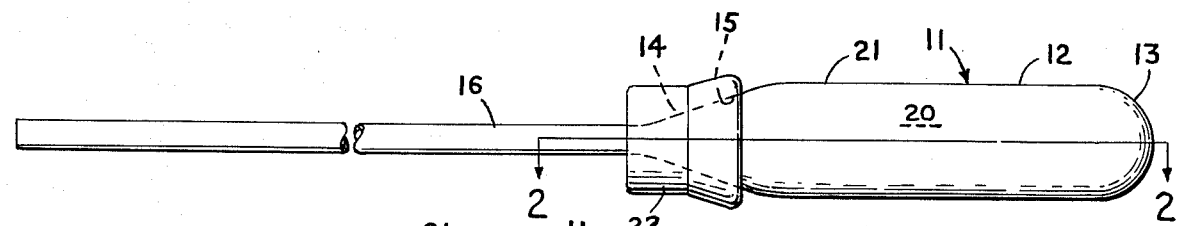
FIG. 1
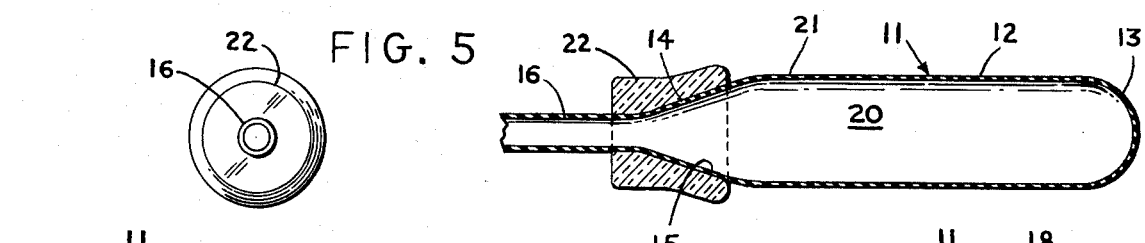
FIG. 5  FIG. 2
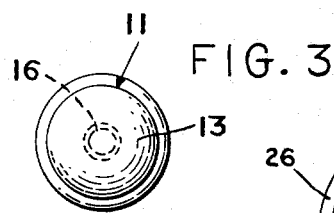
FIG. 3
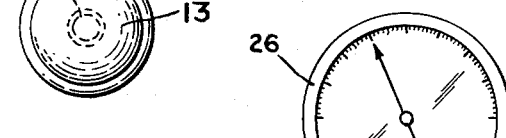
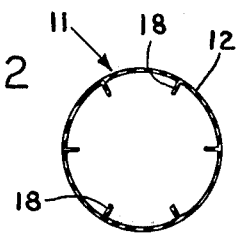
FIG. 6
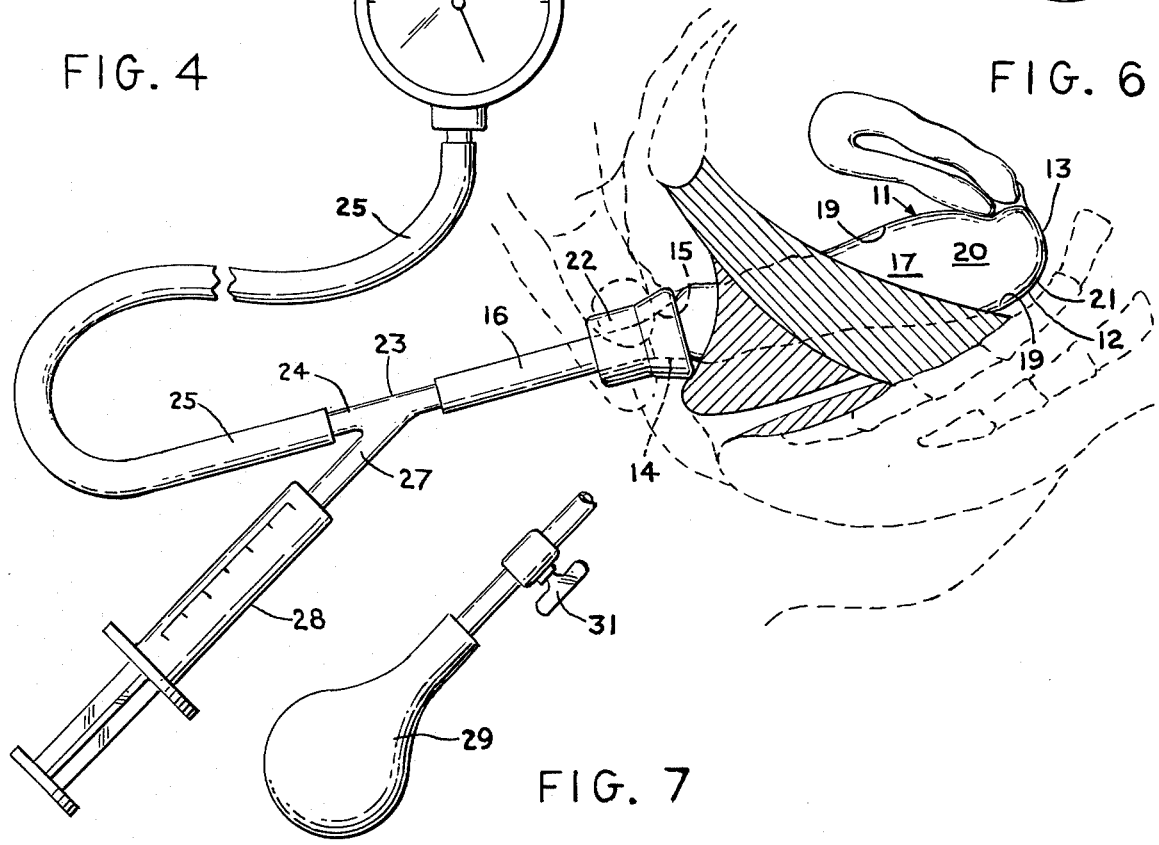
FIG. 7

APPARATUS FOR EXERCISING MUSCLES OF A FEMALE PATIENT'S PELVIC DIAPHRAGM

BACKGROUND OF INVENTION

The vaginal wall is formed essentially of two sets of muscles, one set which extends longitudinally and a second set which encircles the vagina. In addition, those muscles specifically termed the pubococcygenus and levator ani are located immediately adjacent the vagina and have a critical influence on its proper functioning. These muscles have the general appearance of a hammock with its two ends connected to the sides of the pelvis.

Three hollow tube like structures, urethra, vagina and rectum, extend downwardly through respective openings in the central portion of the pelvic diaphragm or hammock. Where the muscle tone of the pelvic diaphragm is good, these openings are maintained constricted through a pulling together action of the muslces of the hammock in concert with the individual sphincters. On deterioration of muscle tone, either through poor physical condition of the individual or injury, these openings in the diaphragm tend to become progressively larger.

It has been found that the physical condition of the vaginal wall muscles, and particularly those forming the pelvic diaphragm, is directly related to the coital responsiveness of a female patient as well as the pleasure received in sexual intercourse. That is, whereas a lax vaginal musculature tends to make the individual relatively unresponsive to the sexual experience, good vaginal muscle tone heightens the effect.

In view of the fact that the muscles comprising the vaginal musculature are, for most individuals, only partially under voluntary control, specific exercise of these muscles for achieving and maintaining their proper conditions to ensure health and well being has been difficult. Accordingly prior art apparatuses, such as those disclosed in U.S. Pat. Nos. 2,507,858 and 2,541,520 both to Kegel, in U.S. Pat. No. 3,640,284 to De Langis and in U.S. Pat. No. 3,752,150 to Harris, have been developed for indicating or observing indirectly, progressive degrees of exercising of injured sphincter muscles for the purpose of developing, reconstructing or regenerating such muscles. The principle of biofeedback upon which these apparatuses are based is that such muscles as may be injured, torn or which require development, are or may be (because of their inherent characteristics, or their anatomical position, or their psysiological function, or because of injury or tearing thereof, for example during childbirth) difficult or impossible to observe or be cognizant of their function which have, to a degree been lost by such injury, tearing or underdevelopment so that it is not possible for the individual to exercise the muscles in a manner so that the muscles may be redeveloped or regenerated through use. It frequently is possible in muscles of this character which have been injured, torn or underdeveloped for the individual to use or operate them, but the individual generally has no realization of the fact, or degree of fact, of the use of such muscles so that it is impossible to determine the fact of their utilization or activation. The regeneration or reconstruction in the development of these muscles is to the greatest degree dependent upon ability of the individual to use the muscles, to exercise them and through exercise and use to develop and reconstruct them.

Kegel's apparatus, known as a Perineometer, is the best known apparatus of this kind. Kegel's apparatus, however, has had limited clinical use, primarily because of lack of patient acceptance. Clinical interviews have uncovered patient complaints about the large size of the sensing member of Kegel's apparatus. This is a factor which contributes both to a patient's physical and phychological discomfort. As with any device designed to be inserted vaginally, two patient psychologic objections must be overcome, phallic fear and masturbatory guilt. Ordinarily physician reassurance helps to allay these objections, but flesh color and penislike stem of the Kegel apparatus aggravate these objections. Multiple parts of the Kegel apparatus make disassembly, cleaning and reassembly a complex task for the patient and this also discourages regular patient use. The intra vaginal portion of the Kegel apparatus is composed of unfinished natural latex, with the result that surface friction characteristics are such that generous amounts of lubricant are required for easy insertion. Harris appears to have made strides toward overcoming disadvantages of the Kegel apparatus. But Harris retains the stem and he left much to be desired by way of structural simplicity.

STATEMENT OF INVENTION

Applicants have overcome problems of the prior art in a useful, novel and unobvious way. They observed that by giving its cylindrical wall sufficient rigidity, the vaginal insert could be inserted conveniently by the patient into her vagina, without need for the offensive stems of the Kegel and Harris apparatuses. By providing a smooth nonwettable outer surface on the vaginal insert, need for lubricant was obviated. Fashioning an unflaired collar or a stiffened tube for manually holding the apparatus in her vagina, enables the patient to close (approximate) her legs while she is exercising.

Accordingly one object of this invention is to reduce psychologic objections of patients to apparatus of this type.

Another object of this invention is to provide an apparatus of this type which is more easily insertable by a patient in her vagina.

Still another object of this invention is to provide an apparatus of this type which is less complex to operate, disassemble, clean and reassemble.

Still another object of this invention is to provide an apparatus of this type which stays more securely in the patient's vagina.

Still another object of this invention is to provide an apparatus of this type which has improved accuracy of pressure measurement.

Still another object of this invention is to simplify patient instruction and minimize need for physician supervision.

Still another object of this invention is to avoid damage to vaginal walls of the patient.

It is still another object of this invention to increase strength and muscle tone of the vaginal wall and associated muscles of the patient.

Still another object of this invention is to provide an apparatus of this type against which the vaginal wall muscles can work as well as can the pubococcygeus and levator ani.

Still another object of this invention is to provide an apparatus of this type which is responsive to both longitudinal and lateral pressures.

Still another object of this invention is to provide an apparatus of this type in which the pressure exerted by the patient on the apparatus can be measured by a fluid such as air or another gas or a liquid at atmospheric or superatmospheric pressure.

Still another object of this invention is to provide an apparatus of this type including a pressure measuring indicator external to the vagina of the patient for indicating a resultant force exerted on the apparatus by the patient.

Still another object of this invention is to provide an apparatus of this type that is well suited otherwise to its intended function.

DESCRIPTION OF DRAWINGS

The foregoing and other objects, features and advantages will appear more fully from a detailed description of preferred embodiments of the invention and from claims, both of which follow, viewed in conjunction with an accompanying drawing wherein like numerals designate like parts throughout and wherein:

FIG. 1 is a side view of an apparatus according to this invention.

FIG. 2 is a sectional view taken along lines 2—2 of FIG. 1.

FIG. 3 is an outer end view of the balloon of this invention.

FIG. 4 is an inner end view of the balloon of this invention.

FIG. 5 shows another and particularly facile embodiment of this invention with a reinforced tube section.

FIG. 6 shows an embodiment of a balloon of this invention with longitudinal ribs projecting inwardly from the cylindrical wall of the balloon.

FIG. 7 illustrates the apparatus according to this invention inserted in a patient's vagina and with pressurizing and pressure measuring apparatus associated operationally therewith.

DESCRIPTION OF PREFERRED EMBODIMENT

As seen in the drawing, the apparatus according to this invention includes a balloon 11 with a substantially cylindrical wall 12 and a first closed end 13 as well as a second end 14 which reduces in section to form a shoulder 15 terminating in a tube 16. The cylindrical wall 12 is provided with sufficient rigidity to permit insertion of the balloon manually into a vagina 17 of a patient with the first end inward as shown in FIG. 7 without need of a central axial stem member. By way of example, using a latex material, a thickness of the cylindrical wall 12 of from 0.035 to 0.070 inches (or 0.89 to 0.178 cm.) provides sufficient rigidity and is otherwise suitable. Alternately the rigidity may be furnished by longitudinal ribs 18 which project inwardly from the cylindrical wall 12 as shown in FIG. 6. It is also important that the cylindrical wall 12 easily engage the vaginal walls 19 of the patient and respond to contractions thereof.

The outer surface 21 of the balloon 11 preferably is provided by known means with a nonwettable smooth finish, so that the balloon 11 can be inserted easily into the patient's vagina 17, without need of a lubricant.

A collar 22 is provided, as shown in FIGS. 1 and 2, to surround the tube 16 and to abut the shoulder 15 so that the patient can hold the balloon in her vagina 17 as shown in FIG. 7. The collar 22 is substantially unflaired to enable the patient to close (approximate) her legs while she is exercising. A reinforcing connector 32 can be used in lieu of the collar 22, as shown in FIG. 5 whereby on approximating her legs, the patient tends to hold the tube 16 in place.

The apparatus can be operated in the same manner as prior art apparatus of this type at atmospheric or superatmospheric pressures with the balloon 11 having its interior 20 filled with air, possibly but not likely with the balloon 11 hving its interior 20 filled with some other gas, or with the balloon 11 being filled with a liquid such as water. As seen in FIG. 7, the balloon 11 terminates at its outer second end 14 in the tube 16 which is adapted to extend out of the patient's vagina 17 and is adapted to receive a bifurcated tube 23 inserted therein. The bifurcated tube 23 has a first fork 24 which communicates via a tube 25 to a pressure gauge 26. A second fork 27 of the bifurcated tube 23 may be communicated in flow series to a syringe 28, if a pressurized liquid is to be used as the fluid in the interior 20 of the balloon 11. Alternately, if pressurized air is to be used in the interior 20 of the balloon 11, a squeeze bulb 29 may be connected to the second fork 27 of the bifurcated tube 23 via a valve 31. If air at atmospheric pressure is to be used as the fluid in the interior 20 of the balloon 11, the bifurcated tube 23 would be replaced by a simple tube (not shown) or the tube 11 could be extended to reach the pressure gauge 26.

It will be obvious to those skilled in manufacture and use of apparatus of this type that wide deviations may be made from the shown and described preferred embodiments, without departing from a main theme of invention set forth in claims which follow.

We claim:

1. Apparatus for exercising and measuring contractile power of muscles of a female patient's pelvic diaphragm, most particularly her vaginal wall muscles; the apparatus comprising:
    an elongated balloon having a substantially cylindrical elastomeric wall and a first closed end,
    the balloon having a second end which reduces in section to form a shoulder and a tube,
    retainer means for the patient to maintain manually the balloon in her vagina,
    the balloon having an interior with a gas therein,
    pressure measuring means connected in flow communication with the interior of the balloon whereby exertions of the patient's vaginal wall and pelvic diaphragm muscles are transmitted through the balloon and the gas and are measured by the pressure measuring means; the apparatus characterized in that the elastomeric cylindrical wall is provided with sufficient rigidity for the balloon to be insertable manually closed endwise uniflated into the patient's vagina.

2. The apparatus of claim 1 further characterized in that the balloon is made of rubber and has a thickness of from 0.035 to 0.070 inches (0.89 to 0.178 cm.).

3. The apparatus of claim 2 further characterized in that the balloon is made of latex and its outer surface is provided with a slick finish.

4. The apparatus of claim 1 further characterized in that the retainer means comprises a collar adapted to surround the tube and abut the shoulder.

5. The apparatus of claim 4 further characterized in that the collar is substantially unflared whereby the patient can close her legs while she is exercising.

6. The apparatus of claim 1 further characterized in that the retainer means comprises a stiffener element for the tube.

7. The apparatus of claim 1 further characterized in that the gas is air.

* * * * *

UNITED STATES PATENT AND TRADEMARK OFFICE
CERTIFICATE OF CORRECTION

PATENT NO. : 4,050,449
DATED : September 27, 1977
INVENTOR(S) : Frank S. Castellana, John C. Byrne, Charles E. Huckaba It is certified that error appears in the above-identified patent and that said Letters Patent are hereby corrected as shown below:

In Column 1, line 20, delete [muslces] and insert muscles therefor.

In Column 2, line 7, delete [phy-] and insert psy- therefor

In Column 4, lines 48-52, same should read as follows:

sure measuring means;

the apparatus characterized in that the elastomeric cylindrical wall is provided with sufficient rigidly for the balloon to be insertable manually closed endwise [uniflated] uninflated into the patient's vagina.

Signed and Sealed this

Seventeenth Day of January 1978

[SEAL]

Attest:

RUTH C. MASON
*Attesting Officer*

LUTRELLE F. PARKER
*Acting Commissioner of Patents and Trademarks*